United States Patent [19]

Ting et al.

[11] Patent Number: 4,880,426
[45] Date of Patent: Nov. 14, 1989

[54] HAPTIC TO OPTIC ATTACHMENT FOR A SOFT IOL

[75] Inventors: Albert C. Ting, Laguna Niguel; Timothy R. Willis, El Toro; F. Richard Christ, Orange; Steven R. Bacich, Irvine; Dean K. Pettit, Irvine; Stanley L. Van Gent, Irvine; Jeffrey C. Day, Mission Viejo, all of Calif.

[73] Assignee: Allergan, Inc., Irvine, Calif.

[21] Appl. No.: 228,709

[22] Filed: Aug. 4, 1988

Related U.S. Application Data

[60] Division of Ser. No. 96,745, Sep. 15, 1987, Pat. No. 4,790,846, which is a continuation of Ser. No. 806,376, Dec. 9, 1985, abandoned.

[51] Int. Cl.⁴ .......................... A61F 2/16; B29D 11/00
[52] U.S. Cl. ........................................... 623/6; 264/1.7
[58] Field of Search ...................... 623/6; 264/1.7, 1.1, 264/2.5

[56] References Cited

U.S. PATENT DOCUMENTS

| | | | |
|---|---|---|---|
| 3,866,249 | 2/1975 | Flom | 623/6 |
| 3,886,600 | 6/1975 | Kahn et al. | 623/21 X |
| 4,150,471 | 4/1979 | Richards et al. | 264/1.7 X |
| 4,338,687 | 7/1982 | Rainin | 623/6 |
| 4,573,998 | 3/1986 | Mazzocco | 623/6 |
| 4,585,454 | 4/1986 | Fabricant | 623/6 |
| 4,615,702 | 10/1986 | Koziol et al. | 623/6 |
| 4,668,446 | 5/1987 | Kaplan et al. | 623/6 X |
| 4,737,322 | 4/1988 | Bruns et al. | 264/1.7 |

FOREIGN PATENT DOCUMENTS

| 516795 | 6/1981 | Australia. | |
|---|---|---|---|
| 2247721 | 9/1972 | Fed. Rep. of Germany | 623/22 |

*Primary Examiner*—Ronald L. Frinks
*Attorney, Agent, or Firm*—Gordon L. Peterson

[57] ABSTRACT

A method of making an intraocular lens including providing a fixation member having a proximal end portion with the proximal end portion including an elongated filament, converting a region of said filament at said proximal end portion from a first configuration into a second configuration which is adapted to provide a mechanical interlock and molding an optic about the proximal end portion of the fixation member to form a mechanical interlock between the second configuration and the optic and to attach the fixation member to the optic.

12 Claims, 2 Drawing Sheets

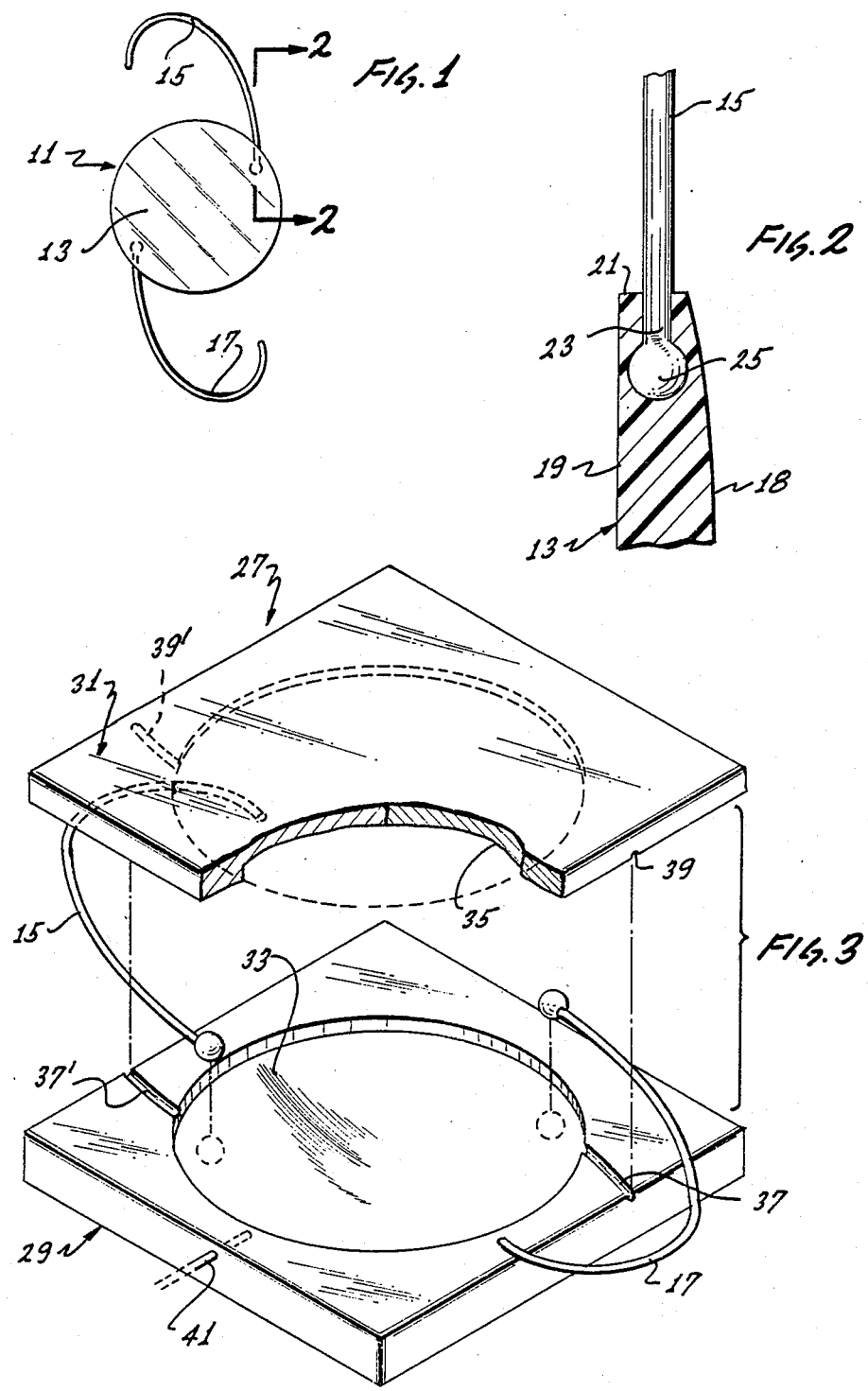

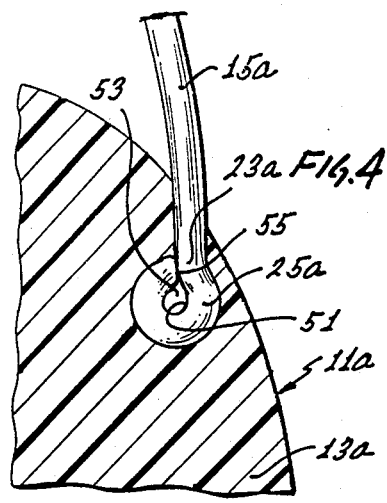
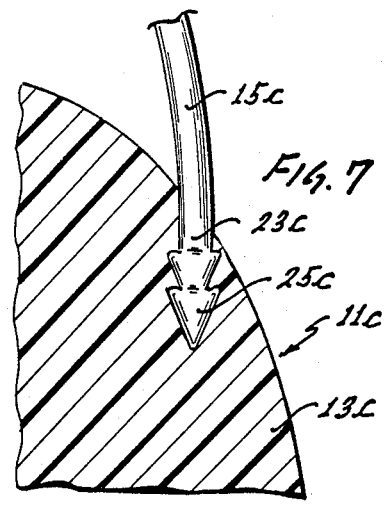
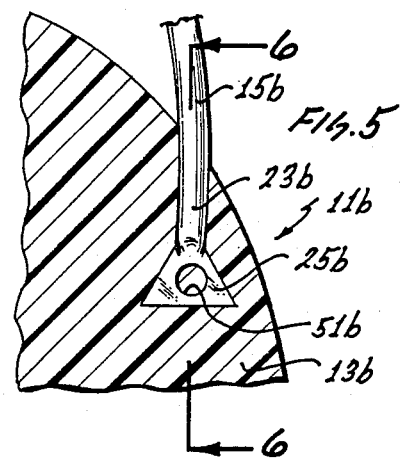
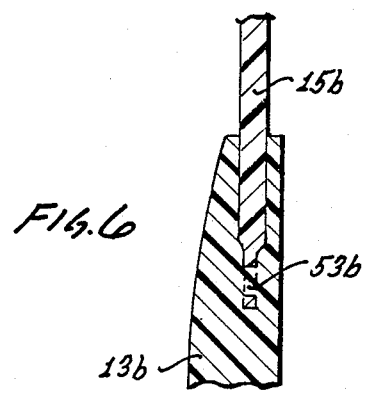
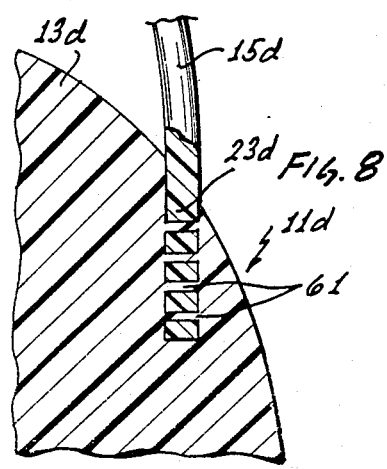
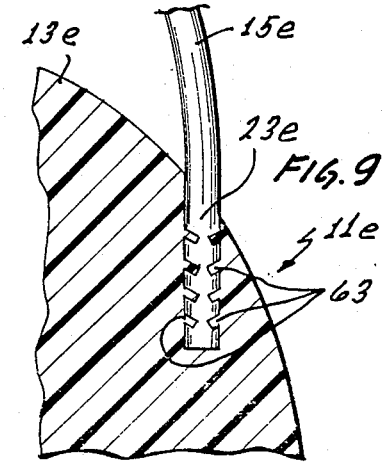

HAPTIC TO OPTIC ATTACHMENT FOR A SOFT IOL

This application is a division of application Ser. No. 096,745 filed on Sept. 15, 1987, U.S. Pat. No. 4,790,846, which is a continuation of application Ser. No. 806,376 filed on Dec. 9, 1985, now abandoned.

BACKGROUND OF THE INVENTION

Intraocular lenses (IOL's) are a well-known type of surgical implant used to replace the natural lens of an eye which has been damaged as a result of trauma or disease. Such IOL'S typically comprise an optic and at least one fixation member attached to the optic. The fixation member functions to position the optic in the correct optical alignment within the eye. Many fixation members are of filamentary form, and are attached to the optic at or near the periphery of the optic.

It is conventional practice to construct the optic of a hard biocompatible polymer, such as polymethylmethacrylate (PMMA). More recently, it has been proposed to construct the optic from a relatively flexible or deformable material. When so constructed, the optic can be rolled or flexed into a relatively small cross-sectional configuration to permit it to be inserted through a relatively small incision into the eye to thereby reduce the trauma and likelihood of infection from the surgery.

The fixation members are constructed of a resilient material, typically polypropylene. In some IOL'S, the fixation members are integrally formed with the optic. In other types of IOL'S, various methods of attaching the fixation members to the optic have been devised.

A common method of attaching requires drilling two small intersecting holes in the edge portion of the optic. A proximal end portion of the fixation member is inserted into one hole and a heated rod is inserted through the other of the intersecting holes. The heated rod melts the proximal end portion of the fixation member where contacted. The fixation member is fed into the hole as the melted material flows into the second intersecting hole, causing a mechanical interlock when the material solidifies. Great precision is required in the drilling of the intersecting holes. Also characteristic of the IOL'S made according to this method is the potential of debris-trapping cavities remaining from a less-than-perfect filling of the holes in the optic by the melted portion of the fixation member.

The attachment of the fixation members to the optic is particularly troublesome when the optic is constructed of soft or deformable materials, such as silicone. When the deformable optic is folded or rolled prior to insertion through the incision into the eye, flexure of the optic creates a likelihood that the fixation member will become detached from the optic. If this occurs, it not only renders the IOL useless, but also is a potential hazard to the patient. The soft optic materials, such as silicone, do not have sufficient rigidity to be used as an integral fixation member or haptic.

It is known to attach the fixation members to a large resilient, circular ring and to mold the soft optic material over the ring so that the ring is concentric with the optic and extends along a peripheral region of the optic. However, for foldable optics, this construction precludes the use of rigid or non-foldable materials for the ring and requires the dedication of a large diameter annulus of the optic to capture the ring.

SUMMARY OF THE INVENTION

This invention solves these problems by molding the optic about a filamentary proximal end portion of the fixation member, which has been permanently deformed into a configuration which is adapted to form a mechanical interlock, to attach the fixation member to the optic. The resulting attachment of the fixation member to the optic is sufficiently strong to preclude separation of the fixation member from the optic even when the optic is constructed of soft, resilient, deformable materials and folded or rolled for insertion through a small incision into the eye.

Although the invention is of particular advantage when used with a deformable optic, it can be used with advantage with either hard or soft optics. Thus, the invention eliminates the need of applying heat and/or pressure to the fixation member while the fixation member is positioned in the optic. As a result, the assembly of the IOL can be accomplished quickly and with precision. In addition, molding of the optic about a proximal end portion of the fixation member eliminates cavities in the optic which are a potential source of debris and bacteria entrapment.

According to the method of this invention, a fixation member is provided which has a proximal end portion, with the proximal end portion including an elongated filament of a first configuration. The filament at the proximal end portion is formed into a second configuration which is different from the first configuration and which is adapted to provide a mechanical interlock. The optic is then molded about the proximal end portion of the fixation member to form a mechanical interlock between the second configuration and the optic and to attach the fixation member to the optic. With this technique, the parent material of the filament is used to form the second configuration which is used to provide the mechanical interlock.

Various configurations can be used to form the mechanical interlock using the parent material of the filament. For example, the configuration may be in the form of an enlargement which is wider than the first configuration. An enlargement has the advantages of providing increased surface area and added strength to the mechanical interlock. Alternatively, or in addition thereto, the interlocking configuration may have an opening therein. This has the advantage that a portion of the optic can be received in the opening to at least partially define a mechanical interlock. The opening can be relatively small and is preferably smaller than the optic and is located at a peripheral region of the optic. The anchoring of the optic to the interlocking configuration in this fashion positively retains the fixation member against rotation in the optic. The opening can be formed, for example, by forming a region of the filament into at least a portion of a loop, by forming an opening in an integral enlargement of the filament and/or by one or more openings or holes which extend through the otherwise unaltered filament.

When the enlargement is used, it can be formed in various different ways. For example, a region of the proximal end portion can be heated to form a bulbous enlargement from the material of the filament, and the enlargement is then solidified by cooling. Alternatively, a region of the proximal end portion of the filament can be heated to permit it to be permanently deformed, or bent into various different configurations, such as an arc or loop defining the opening. Alternatively, an enlargement can be formed by heating an end portion of the filament in a mold of the desired configuration.

If the interlocking configuration is to be provided without an enlargement, this can be accomplished, for example, by removing material from a region of the proximal end portion of the fixation member. Material removal can be accomplished, for example, by drilling or milling. Of course, any desired number of fixation members can be attached to the optic using the teachings of this invention.

The invention, together with additional features and advantages thereof, may best be understood by reference to the following description taken in connection with the accompanying illustrative drawing.

BRIEF DESCRIPTION OF THE DRAWING

FIG. 1 is a front elevational view of an IOL constructed in accordance with the teachings of this invention.

FIG. 2 is an enlarged, fragmentary, sectional view taken generally along line 2—2 of FIG. 1.

FIG. 3 is an exploded isometric view of a portion of a mold and two of the fixation members, with the mold being shown somewhat diagrammatically.

FIGS. 4–9 are enlarged, fragmentary, sectional views illustrating portions of optics and fixation members with the fixation members having proximal end portions of different configurations.

DESCRIPTION OF THE PREFERRED EMBODIMENTS

FIG. 1 shows an IOL 11 which comprises an optic 13 of a transparent, biocompatible materials and fixation members 5 and 17. Although the optic 13 could be of various different configurations, in the embodiment illustrated, it has a convex anterior face 18 (FIG. 2), a planar posterior face 19, and a cylindrical periphery or edge 21. The optic 13 may be constructed of any hard or soft material suitable for use in an optic. For example, the optic may be constructed of a relatively hard material, such as PMMA, or soft, deformable materials, such as silicone and polyurethane, which permit the optic 13 to be rolled or folded into a smaller configuration for insertion through a relatively small incision into the eye.

The fixation members 15 and 17 retain or fix the optic 13 in the correct position within the eye. Each of the fixation members 15 and 17 is in the form of an elongated, resilient strand or filament. Although the fixation members can be of various different configurations, in this embodiment, they are each of a generally J-shaped configuration, and they are constructed of a resilient, biocompatible material, such as polypropylene.

The fixation member 15 has a proximal end portion 23 which is embedded within a peripheral region of the optic 13. The fixation member 15 has a configuration which is adapted to form a mechanical interlock and which, in this embodiment, is in the form of a bulbous enlargement 25 at the proximal end of the fixation member. The bulbous enlargement 25 forms a portion of the proximal end portion 23.

The optic 13 is cast about the proximal end portion 23 to securely attach the fixation member 15 to the optic 13. The bulbous enlargement 25 cooperates with the optic 13 to form a mechanical interlock which strongly interlocks the fixation member 15 to the optic so that rolling, folding or flexing of the optic 13 (when it is constructed of resilient, deformable materials) will not bring about detachment of the fixation member from the optic. Because the optic 13 is cast about the proximal end portion 23 of the fixation member 15, there are no cavities or openings in the optic as a result of the attachment of the fixation member to the optic. Of course, conventional manipulation apertures may be provided in the optic 13, if desired. The fixation member 17 is identical, in the illustrated embodiment, to the fixation member 15 and is identically attached to the optic 13 at a diametrically opposed location on the optic.

The enlargement 25 has a cross-sectional area which is larger than that of the remainder of the proximal end portion 23. The material of the optic 13 intimately contacts all surfaces of the proximal end portion 23 of the fixation member so the fixation member is firmly embedded in the optic.

The fixation member 15 and the proximal end portion 23 thereof are initially in a cylindrical configuration. A region of the proximal end portion 23 can be most easily permanently deformed into a second or interlocking configuration, i.e., the enlargement 25, which is wider than the original cylindrical configuration, by heating the proximal end portion 23, or a region thereof, to a temperature sufficient to cause it to flow to form the bulbous-shaped enlargement 25. This may be accomplished, for example, by a small flame or a $CO_2$ or Nd.:YAG laser. After heating, the molten thermoplastic material is cooled to solidify it. The enlargement 25 is formed before the optic 13 is cast about the proximal end portion 23. If desired, the enlargement 25 may have its outer surface roughened to improve adhesion of the material of the optic 13.

FIG. 3 shows a mold 27 of the type which may be used for insert molding of the optic 13 about the proximal end portions of the fixation members 15 and 17. The mold 27 includes a bottom mold half 29 and a top mold half 31. The mold halves 29 and 31 include mold cavities 33 and 35, respectively, whose surfaces correspond to the anterior and posterior faces 18 and 19 of the optic 13 to be molded. The perimeter edges of the mold cavities 33 and 35 are aligned with one another, and the parting line thus formed extends along the cylindrical edge 21 of the optic 13. A slot 37 runs from the side of the mold half 29 and intersects the perimeter edge of the cavity 33. Another slot 39 in the mold half 31 matches with the slot 37 and similarly intersects its corresponding mold cavity 35. As the fixation member 17 which is to be positioned in slots 37 and 39 is generally cylindrical in cross section, each of the slots 37 and 39 approximates a hemicylinder or a rectangular channel. Where other fixation member configurations are contemplated, the shape or shapes of the slots 37 and 39 should be such as to hold the fixation member in proper position while minimizing leakage of the molding material and the formation of flash resulting from such leakage. Corresponding slots 37' and 39' are provided in the mold halves 29 and 31, respectively, for the fixation member 15. While the mold 27 is shown as capable of molding and assembling a single IOL, the principles of this invention can be applied to operations which mold a plurality of IOL'S simultaneously.

In operation, fixation members 15 and 17, complete with the proper-sized enlargements 25 on their proximal end portions, are positioned in alignment with slots 37', 39' and 37, 39, respectively. The mold halves 29 and 31 are closed. The selected optical material is injected into the closed cavity via a screw hole 41 using conventional injection molding or casting techniques. The material is permitted to cure by chemical reaction, and then the mold halves 29 and 31 are opened to provide a completed molded and assembled IOL which requires only minimal deflashing.

The mechanical keying of the enlargement 25 to the optic 13 is anticipated to be adequate in resisting pull-out forces even when soft or resilient materials are used for the optic. However, separate adhesives and/or adhesive characteristics of certain materials could be used to augment the attachment between fixation members 15 and 17 and the optic 13.

FIGS. 4-6 show IOL'S 11a and 11b, and each of these IOL'S is identical to the IOL 11 in all respects not shown or described herein. Portions of the IOL'S 11a and 11b corresponding to portions of the IOL 11 are designated by corresponding reference numerals followed by the letters "a" and "b", respectively.

The IOL 11a differs from the IOL 11 in that the fixation member 15a has a region of its proximal end portion 23a permanently bent or deformed into an enlargement 25a in the form of a loop. The enlargement 25a is formed into a loop of generally circular configuration and defines an opening 51 which has a portion 53 of the optic 13a cast therein to form a strong mechanical interlock which locks the fixation member 15a against rotation in the optic. The enlargement 25a is formed, for example, by heating a region of the proximal end portion 23a, which is originally of a cylindrical configuration, to make the material of the fixation member 15 permanently deformable, and forming the region into a loop or second configuration, and allowing the loop to cool whereby a region of the fixation member is permanently deformed. If desired, the loop 25a may be welded closed, as by ultrasonic bonding, to the fixation member 15 at the outer end 55 of the loop. Of course, the region of the proximal end portion 23a can be formed into enlargements 25a of different configurations by simply bending of such region into such configuration. The other fixation member may be similarly attached to the optic 13a.

The enlargement or loop 25a has its broadest dimensions in the broad plane of the optic 13a. The opening 51 may be very small, e.g., of the order of one or more diameters of the fixation member 15a, and it is located at a peripheral region of the optic. Consequently, the enlargement or loop 25a does not interfere with the folding of the optic 13a when the latter is constructed of a soft material. Of course, the optic 13a can be cast about the proximal end portion 23a as described above.

The IOL 11b is similar to the IOL 11a, except that the enlargement 25b is formed by deforming a region of the fixation member 15b into a flat, generally triangular tab having an opening 51b therein. Although the flat tab also constitutes a loop, the loop is not formed by bending of a region of the proximal end portion of the fixation member as shown in FIG. 4 but rather by, for example, heating the material of the proximal end portion 23b in a die so as to cause it to assume the shape shown. Of course, other shapes that will interlock with the material of the optic 13b can be used. A portion of the material 53b of the optic 13b extends through the opening 51b as best shown in FIG. 6 to form a strong mechanical interlock which locks the fixation member 15b against rotation in the optic.

The IOL 11c (FIG. 7) differs from the IOL 11 in that the enlargement 25c includes multiple barbs. The enlargement 25c may be formed, for example, by heating a region of the proximal end portion 23c in a mold.

In all of the illustrated embodiments of the invention, a region of the proximal end portion is converted from an original configuration into a configuration which is capable of forming a mechanical interlock. In the IOL'S 11d and 11e (FIGS. 8 and 9), the proximal end portions 23d and 23e are provided with a configuration which is capable of forming a mechanical interlock, but the enlargement 25 of the IOL 11 is eliminated. Rather, in the IOL'S 11d and 11e, material is removed from the proximal end portions 23d and 23e to provide an irregular configuration and to increase the surface area of contact with the material of the optic. In the IOL 11d, the proximal end portion 23d is drilled to form a plurality of cavities or bores 61 extending through the proximal end portion into which the material of the optic 13d can flow during molding to provide a strong mechanical interlock which also resists rotation of the fixation member 15d. In the IOL 11e, the proximal end portion 23e has been milled to form a plurality of outwardly opening cavities in the form of slots 63 into which the material of the optic 13e can flow during molding of the optic to form a strong mechanical interlock which also resists rotation of the fixation member 15e. Preferably the slots 63 open in a direction to resist pull out of the fixation member 15e as shown in FIG. 9, i.e., open in a direction such that the surfaces defining the slots 63 tend to dig into the optic if the fixation members are subjected to an outward pulling force.

Although FIGS. 4-19 illustrate only one of the fixation members, any number of the fixation members can be attached to the optic as shown therein. Furthermore, an IOL can be provided in which each of the fixation members is attached to the optic in accordance with a different illustrated embodiment of the invention.

Although exemplary embodiments of the invention have been shown and described, many changes, modifications and substitutions may be made by one having ordinary skill in the art without necessarily departing from the spirit and scope of this invention.

We claim:

1. An intraocular lens comprising:
   at least one fixation member having a proximal end portion, said proximal end portion including a filament and a bulbous configuration coupled to the filament and adapted to form a mechanical interlock; and
   an optic cast about said bulbous configuration and the proximal end portion to form a mechanical interlock between said bulbous configuration and the optic and to attach the fixation member to the optic.

2. An intraocular lens as defined in claim 1 wherein said bulbous configuration is formed from parent material of the fixation member.

3. An intraocular lens as defined in claim 1 wherein said optic can be flexed to permit it to be inserted through a relatively small incision into the eye.

4. An intraocular lens as defined in claim 1 wherein the optic is devoid of openings as a result of the attachment of the fixation member to the optic.

5. An intraocular lens as defined in claim 1 wherein the fixation member extends from the optic generally in the plane of the optic.

6. An intraocular lens as defined in claim wherein the optic is flexible and the optic is devoid of openings as a result of the attachment of the fixation member to the optic.

7. A method of making an intraocular lens comprising:
- providing a fixation member having a proximal end portion with the proximal end portion including an elongated filament of a first configuration;
- forming a region of said filament at said proximal end portion into a bulbous enlargement which is different from said first configuration and which is adapted to provide a mechanical interlock; and
- molding an optic about the proximal end portion of the fixation member to form a mechanical interlock between said bulbous enlargement and the optic and to attach the fixation member to the optic.

8. A method as defined in claim 7 wherein said step of forming includes heating said region of the filament to form said bulbous enlargement.

9. A method as defined in claim 1 wherein said step of molding includes molding a deformable optic about said proximal end portion of the fixation member.

10. A method as defined in claim 7 wherein said step of molding is carried out without forming openings in the optic as a result of the attachment of the fixation member to the optic.

11. A method as defined in claim 7 wherein said step of molding is carried out to that the fixation member extends from the optic generally in the plane of the optic.

12. A method as defined in claim 11 wherein the optic is deformable and said step of molding is carried out without forming openings in the optic as a result of the attachment of the fixation member to the optic.

* * * * *

UNITED STATES PATENT AND TRADEMARK OFFICE
CERTIFICATE OF CORRECTION

PATENT NO. : 4,880,426

DATED : Nov. 14, 1989

INVENTOR(S) : Albert C. Ting et al

It is certified that error appears in the above-identified patent and that said Letters Patent is hereby corrected as shown below:

On the title page:

Please delete the following inventors:

Dean K. Pettit
      Jeffrey C. Day
      Stanley L. Van Gent
      Timothy R. Willis
      Richard Christ Column 2, line 66 after "deformed" delete the period.

Column 3, line 33 change "materials" to -- material --.

Column 3, line 34 change "5" to -- 15 --.

Column 6, line 29 change "4-19" to -- 4-9 --.

Column 6, line 65 change "as defined in claim" to -- as defined in claim 5 --.

UNITED STATES PATENT AND TRADEMARK OFFICE
CERTIFICATE OF CORRECTION

PATENT NO. : 4,880,426

DATED : November 14, 1989

INVENTOR(S) : Albert C. Ting, et al

It is certified that error appears in the above-identified patent and that said Letters Patent is hereby corrected as shown below:

Column 8, line 1, change "claim 1" to --claim 7--.

Column 8, line 9, change "out to" to --out so--.

Signed and Sealed this

Twelfth Day of March, 1991

Attest:

HARRY F. MANBECK, JR.

*Attesting Officer*      *Commissioner of Patents and Trademarks*